United States Patent
Inada et al.

(10) Patent No.: US 7,030,264 B1
(45) Date of Patent: Apr. 18, 2006

(54) BIS-β-HYDROXYETHYL TEREPHTHALATE

(75) Inventors: Shuji Inada, Tokyo (JP); Kikuchi Sato, Fukuyama (JP)

(73) Assignee: Aies Co. Ltd., Tokyo (JP)

( * ) Notice: Subject to any disclaimer, the term of this patent is extended or adjusted under 35 U.S.C. 154(b) by 0 days.

(21) Appl. No.: 10/333,996

(22) PCT Filed: Jul. 31, 2000

(86) PCT No.: PCT/JP00/05148

§ 371 (c)(1),
(2), (4) Date: Jan. 24, 2003

(87) PCT Pub. No.: WO02/10117

PCT Pub. Date: Feb. 7, 2002

(51) Int. Cl.
C07C 69/76 (2006.01)
C07C 67/48 (2006.01)
C07C 67/00 (2006.01)
C07C 67/14 (2006.01)

(52) U.S. Cl. ............ 560/76; 560/78; 560/89; 560/96; 560/98

(58) Field of Classification Search .......... 560/76, 560/89, 96, 98, 78
See application file for complete search history.

(56) References Cited

U.S. PATENT DOCUMENTS

| | | | | |
|---|---|---|---|---|
| 3,776,945 A | * | 12/1973 | Ligorati et al. | 562/483 |
| 5,476,919 A | | 12/1995 | Schaeffer | 528/272 |
| 5,672,729 A | * | 9/1997 | Naujokas | 560/78 |
| 5,750,776 A | * | 5/1998 | Harvie | 562/483 |
| 5,869,543 A | * | 2/1999 | Boos et al. | 521/48.5 |

FOREIGN PATENT DOCUMENTS

| | | |
|---|---|---|
| EP | 0723951 A1 * | 1/1996 |
| EP | 1 120 394 A1 | 8/2001 |
| EP | 1 254 888 A1 | 11/2002 |
| GB | 1143072 * | 2/1969 |
| GB | 1344487 * | 1/1974 |
| JP | 50-89340 | 7/1975 |
| JP | 2000-053802 | 2/2000 |
| JP | 2000-159729 | 6/2000 |
| JP | 2000-169623 | 6/2000 |
| JP | 2000-191593 | 7/2000 |
| JP | 2000-239233 | 9/2000 |

OTHER PUBLICATIONS

1–page PCT Form IB/338 with attached 6–page PCT Form IPEA/409 (International Preliminary Examination Report) in English.
European Search Report for EP 00 94 8347 citing above two references.

* cited by examiner

Primary Examiner—Ba K. Trinh
Assistant Examiner—Taylor V. Oh
(74) Attorney, Agent, or Firm—Anderson Kill & Olick, P.C.; Eurgene Lieberstein; Michael N. Meller

(57) ABSTRACT

Bis-β-hydroxyethyl terephthalate having an optical density measured in a 10 wt % methanol solution at a measurement wavelength of 380 nm and a cell optical path length of 10 mm of 0.000 to 0.006. The present invention makes it clear that purified BHET having an optical density of 0.006 or less provides high-quality PET having excellent purity, whiteness and transparency.

2 Claims, 1 Drawing Sheet division purification process diagram

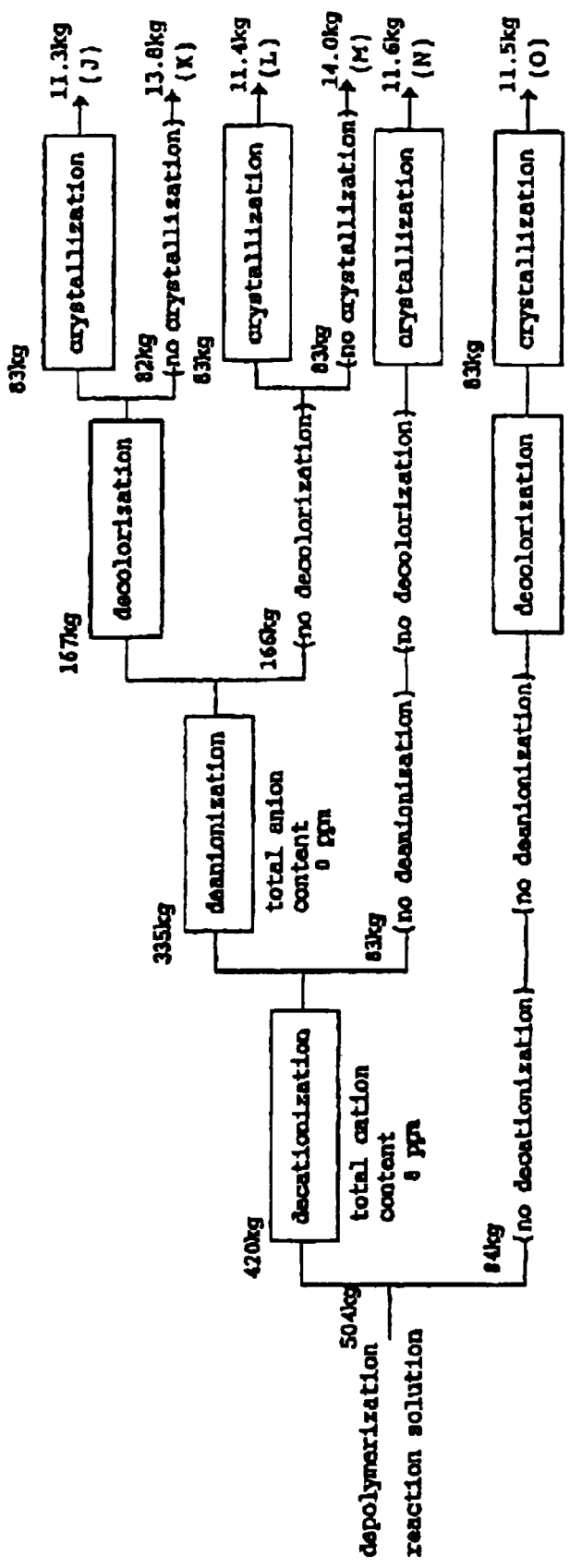

BIS-β-HYDROXYETHYL TEREPHTHALATE

DETAILED DESCRIPTION OF THE INVENTION

1. Field of the Invention

The present invention relates to purified bis-βhydroxyethyl terephthalate (to be abbreviated as BHET hereinafter) and to a process for producing an aromatic polyester, particularly polyethylene terephthalate (to be abbreviated as PET hereinafter) from the same. BHET is widely used in the industrial field as a raw material for PET which is an extremely useful polyester in the field of molded products such as fibers, films and resins.

2. Prior Art

Polyesters, particularly polyesters comprising ethylene terephthalate as the main ingredient are widely used for various purposes as described above. Production processes for these polyesters which are now put into practice include one in which a polyester is obtained through direct esterification between terephthalic acid and ethylene glycol or one in which an intermediate containing BHET is obtained from an ester exchange reaction between a lower alkyl ester of terephthalic acid, especially dimethyl terephthalate, and ethylene glycol and polycondensed at a high temperature under high vacuum. The application of polyesters has recently been diversified based on their excellent performance. Therefore, requirements for high quality are being diversified and advanced.

Aromatic polyesters are basically produced by increasing the degree of polymerization by making metal compounds existent as polymerization catalysts at a high temperature under high vacuum and maintaining them in a molten state for a long time. It is not easy to satisfy all the requirements for polyesters. Therefore, as means of improving the quality of a polyester by satisfying various requirements, various methods have been proposed as below, in addition to an increase in the purities of raw materials: (1) a new comonomer is added to a polyester, (2) a polymerization catalyst is improved, and (3) various additives are added. However, these methods cannot satisfy all the requirements.

SUMMARY OF THE INVENTION

The inventor of the present invention has conducted various studies under the notion that the qualities of polyester raw materials should be basically improved to substantially obtain a high-quality polyester and that the above means to improve the quality of a polyester are auxiliary means to be employed as required. As for the purification of terephthalic acid or dimethyl terephthalate which is a lower alkyl ester thereof, as a raw material for a polyester, various proposals have been made. However, practical means of improving the quality of BHET as a raw material or intermediate close to the final polymer has not been found yet. It is an object of the present invention to provide high-quality purified BHET which could not be obtained in the prior art, thereby providing extremely useful means of obtaining a higher quality polyester than a polyester produced from conventional high-purity terephthalic acid or dimethyl terephthalate.

That is, the above object of the present invention can be attained by bis-β-hydroxyethyl terephthalate having (i) an optical density of 0.000 to 0.006 measured in a 10 wt % methanol solution at a measurement wavelength of 380 nm and a cell optical path length of 10 mm, (ii) cation content of 15 ppm or less, (iii) anion content of 1 ppm or less and (iv) purity of 98 wt % or more. Typically, the high-quality purified BHET is obtained by a process for producing bis-β-hydroxyethyl terephthalate, comprising steps (i) depolymerizing a collected post-consumer polyethylene terephthalate with ethylene glycol to form depolymerized products containing bis-β-hydroxyethyl terephthalate, (ii) carrying out decationization and/or deanionization for the depolymerized products formed in the step (i) to form deionized products having total content of cations and anions of 40 ppm or less and (iii) carrying out molecular distillation for the deionized products formed in the step (ii) at 130 to 250° C. under a pressure 300 Pa or less. More typically, the purified BHET is provided by (1) crystallizing crude BHET having a total content of the above cations and anions of 50 ppm or less from a solvent and (2) purifying the crystallized BHET by evaporation or distillation under reduced pressure.

BRIEF DESCRIPTION OF THE DRAWINGS

FIG. 1 is a diagram showing a purification process for obtaining six different compositions containing crude BHET as the main ingredient (Examples 5 to 9 and Comparative Example 1).

DETAILED DESCRIPTION OF THE EMBODIMENT

The present invention will be described in detail hereinafter.

Crude BHET as a raw material for purified BHET to which the present invention is directed may be produced by any process. For example, it may be produced by reacting terephthalic acid or dimethyl terephthalate with ethylene glycol or by addition reacting terephthalic acid with ethylene oxide. These processes use so-called PET monomers as raw materials.

Meanwhile, there is a process for producing crude BHET by adding an excessive amount of ethylene glycol to PET or an oligomer thereof (low condensate) as a raw material to carry out a depolymerization reaction. PET may be recovered as a modified product such as a fiber, film or bottle. As a starting material, the recovered molded product is preferred and advantageous from an environmental point of view and also a financial point of view. The present invention has been made to solve mainly technical problems in quality and a production process caused by the use of these recycled products as a raw material.

There have been made proposals for improving the quality of crude BHET by recrystallization operation and not evaporation or distillation. However, the quality of BHET is apparently improved by the above technique but actually impurities which are harmful in practical use remain and become a barrier to the acquisition of a high-quality polyester in many cases. Particularly when a polyester is to be obtained from BHET prepared by collecting a used polyester and depolymerizing it with ethylene glycol, bad effects caused by foreign matter adhered to or accompanied by a used polyester product are markedly seen in many cases. Meanwhile, there has been made a proposal for obtaining purified BHET by evaporation or distillation purification. In this case, when crude BHET is subjected to evaporation or distillation operation, a condensation reaction which causes a problem occurs markedly, thereby making it difficult to practically obtain high-quality BHET with high efficiency in high yield.

According to the results of studies conducted by the present inventors, the bad effects caused by the evaporation or distillation of BHET can be substantially suppressed by combining decationization and/or deanionization with decolorization as required before evaporation or distillation operation, further substantially removing substances having a lower boiling point than BHET and then evaporating or distilling crude BHET at a temperature range and a reduced pressure at which BHET hardly deteriorates in quality, for example, 130 to 250° C. and 300 Pa (2.25 mmHg) or less. Further, prior to evaporation or distillation under reduced pressure, BHET is crystallized from a solvent a required number of times to obtain purified BHET which is extremely suitable for obtaining a high-quality polyester. According to the results of studies conducted by the present inventors, it is important to pay close attention to each operation to avoid contamination, keep the atmosphere clean and make it an inert atmosphere, thereby making it possible to obtain high-quality purified BHET of the present invention. Surprisingly, a polyester having excellent transparency and whiteness is obtained from the obtained purified BHET of the present invention. This will be detailed in the section of Examples.

To substantially obtain the purified BHET of the present invention from crude BHET, evaporation or distillation is carried out under reduced pressure. The evaporation or distillation of the crude BHET may be boiling-point evaporation or distillation which is carried out at an evaporation or distillation temperature and pressure, namely, equilibrium evaporation or distillation, or non-equilibrium evaporation or distillation that one-way shift from an evaporation plane to a condensation plane occurs without the return of the evaporated molecules of BHET to an evaporation plane, namely, so-called molecular distillation. Therefore, use of a high-vacuum evaporator or distiller suitable for the above is desired and a distiller called "thin film distillers" or "molecular distillers" which is rarely damaged by pressure is preferred.

In the present invention, before the above evaporation or distillation operation is carried out, it is desired that crude BHET to be subjected to evaporation or distillation operation should be substantially decationized and/or deanionized and subjected to a decolorization step or crystallization step as required and that substances having a lower boiling point than BHET should be completely removed in order to increase the yield and quality of purified BHET to more practically advantageous levels.

In this case, crude BHET which has been deionized to such an extent that the total content of cations consisting of (i) Na, Mg, Ca, Fe, Co, Zn, Ti, Sn, Sb, Ge and P and (ii) anions consisting of halogen, $NO_2$, $NO_3$, $PO_4$ and $SO_4$ is 50 ppm or less is preferably used as the crude BHET.

Cations and anions as impurities contained in the crude BHET are mainly derived from a polyester polymerization or depolymerization catalyst, stabilizer, modifier and colorant added to molded products, or pollutants and are mostly in the form of metal compounds.

These cations or anions are generally contained in BHET in an amount of several hundreds to several thousands of ppm, prevent the implementation of the above-described existing processes for obtaining BHET (recrystallization process and evaporation or distillation process) and are one of the causes of a failure to obtain high-quality PET.

BHET which has been deionized to such an extent that the total content of these cations and anions is 40 ppm or less is preferably used as the BHET of the present invention before evaporation or distillation. The total content of cations and anions is more preferably 30 ppm or less, the most preferably 20 ppm or less.

In the present invention, the contents of cations and anions in BHET are measured by inductive coupling plasma emission spectral analysis (ICP-AES) and ion chromatography, respectively.

To adjust the total content of cations and anions to the above specific range, deionization using an ion exchanger, particularly an ion exchange resin is preferred. In this case, it is practical to carry out decationization and/or deanionization in a solution containing ethylene glycol as the main solvent and BHET as the main solute. The decationization may be carried out before or after the deanionization. They may be carried out several times as required. An example of the ion exchange resin for decationization is an amberlite cation exchange resin (of Organo Co., Ltd.) and an example of the ion exchange resin for deanionization is an amberlite anion exchange resin (of Organo Co. Ltd.). The deionization step using the ion exchange resin can be carried out by a known method per se. Preferably, the temperature condition and the concentration of BHET in a solution containing ethylene glycol as the main solvent and BHET as the main solute which ensure that BHET is not precipitated in the solution and can stand the stable use of the ion exchange resin are selected to carry out decationization and/or deanionization operation.

In the present invention, the crystallization step for extracting BHET as crystals is preferably carried out more than 1 time as described above. The step of extracting BHET as crystals is carried out under conditions for controlling the concentration of BHET in a solution containing ethylene glycol as the main solvent and BHET as the main solute such that a solution state is maintained at a high temperature range and BHET separates out at a low temperature range. It is generally possible to control the high-temperature condition for maintaining a solution state within the heat resistance temperature of the ion exchange resin in the above described deionization step.

It is desired that the crude BHET used in the evaporation or distillation purification step of the present invention should have a total ion content in the above range and contain substances having a lower boiling point than BHET in an amount of preferably 5 wt % or less, more preferably 2 wt % or less, much more preferably 1 wt % or less.

When the above-described specific crude BHET used in the present invention and crude BHET which is generally existent and does not satisfy the requirements of the present invention are placed under the same conditions, they completely differ from each other in behavior. For example, when crude BHET having a total cation content of 2,080 ppm and a total anion content of 22 ppm was concentrated until the total content of substances having a lower boiling point than BHET became 5.0 wt % or less and distilled under high vacuum without carrying out decationization and deanionization, the obtained BHET was strongly colored to such an extent that it could be visually recognized apparently, the formation rate of an oligomer during distillation was high at about 10%, the precipitate was adhered to or accumulated on the heat transfer surface of a distiller, preventing stable heat transfer at the time of distillation, and the recovery of BHET was about 70% or less. Meanwhile, when crude BHET which has been deionized by carrying out decationization and deanionization to reduce the total cation content to 15 ppm or less and the total anion content to 1 ppm or less was concentrated under the same conditions after the step of extracting it as crystals and distilled under high vacuum under the same conditions, the coloring of the obtained BHET was not observed visually, the formation rate of an oligomer during distillation was about 1%, and the precipitate was rarely fixed to the heat transfer surface of the distiller, thereby making possible stable continuous operation, and the recovery of BHET was about 98% or more.

In the present invention, before or after the deionization of BHET to be evaporated or distilled is carried out, it is desirable that the crude BHET should be decolorized in an ethylene glycol solution. A treatment with an adsorber such as activated carbon is advantageous as decolorization. This decolorization can be carried out in combination with the BHET crystallization step. The decolorization is carried out under such temperature and concentration conditions that BHET does not separate out in an ethylene glycol solution of BHET. BHET is collected under such temperature and concentration conditions that BHET separates out.

In the present invention, the temperature at which BHET is evaporated or distilled under reduced pressure is preferably in the range of 130 to 250° C., more preferably 160 to 220° C. The pressure is preferably 300 Pa (2.25 mmHg) (absolute pressure) or less, more preferably 70 Pa (0.5 mmHg) (absolute pressure) or less.

The purified BHET obtained by evaporation or distillation purification of the present invention has extremely high quality and an optical density of 0.000 to 0.006 measured in a 10 wt % methanol solution at a measurement wavelength of 380 nm and a cell optical path length of 10 mm. This high-quality purified BHET has been totally unknown in the prior art. The purity of the BHET is preferably 97 wt % or more, more preferably 98 wt % or more, and most substances other than BHET are terephthalic acid compounds which are useful as constituents of a polyester and do not substantially cause a reduction in the quality of a polyester.

The purified BHET obtained by the present invention is advantageously used alone or mixed with terephthalic acid as at least one of raw materials for a polyester widely used for various purposes as described above. It has been found that when a polyester is formed from the purified BHET of the present invention, it is a non-colored polymer having extremely excellent transparency and whiteness. This is a surprising result and the purified BHET of the present invention has an extremely high industrial value. Although an antimony compound or germanium compound known per se can be used as a polymerization catalyst, it is needless to say that additives should be selected very carefully to exhibit the feature of the polymerization catalyst to a full extent and not to reduce the feature.

The polyester comprises ethylene terephthalate as the main constituent unit and encompasses a copolymer comprising a small amount of at least one other constituent component. The allowable amount of the other constituent component is generally 40 mol % or less, preferably 30 mol % or less, more preferably 20 mol % or less based on the total of all the constituent units. Examples of dicarboxylic acid component as the other constituent component copolymerizable include aromatic dicarboxylic acids such as isophthalic acid, diphenyldlcarboxyllc acid, diphenylsulfonedlcarboxyllc acid, diphenyl ether dicarboxylic acid, naphthalenedicarboxylic acid, diphenoxyethane dicarboxylic acid and sodium sulfoisophthalic acid, aliphatic dicarboxyllc acids such as sebacic acid and adipic acid, and alicyclic dicarboxylic acids such as hexahydroterephthalic acid. Examples of diol component as the other constituent component copolymerizable include trimethylene glycol, tetramethylene glycol, hexamethylene glycol, cyclohexane dimethanol, bis-β-hydroxyethyl bisphenol A, bis-β-hydroxyethoxydiphenyl sulfone, bis-β-hydroxyethoxydiphenyl ether, diethylene glycol, polyethylene glycol and the like. Hydroxycarboxylic acids such as p-hydroxyethoxyphenyl carboxylic acid may be used as the other copolymerizable component. Further, a polyfunctional compound having a functionality of 3 or more and/or a monofunctional compound may also be used as the other copolymerizable component. These components may be used in limits that the polyester keeps linear. Examples of the polyfunctional compound having a functionality of 3 or more include trimesic acid, glycerin, pentaerythritol and the like, and examples of the monofunctional compound include diphenylmonocarboxylic acid, diphenyl ether monocarboxylic acid, phenoxypolyethylene glycol and the like. These copolymerizable components may be used as a functional derivative such as an ester. They may be used alone or in combination of two or more.

According to the result of studies conducted by the present inventors, a polyester obtained by using the purified BHET obtained by the present invention as at least one of its raw materials can be used as a molded product such as a fiber, film or bottle without a problem. Further, these polyester molded products can be depolymerized again to obtain purified BHET, that is, can be recycled easily. In this case, according to the process of the present invention, high-quality BHET specified by the present invention can be obtained.

According to the present invention, even when a polyester to be depolymerized is mixed with another material or foreign matter such as dust in the case of a molded product such as a commercial product, the foreign matter removing and separation step is applied as required to obtain crude BHET which can be used in the present invention.

Giving specific examples, when the polyester molded product is a fibrous commercial product, BHET may be mixed with a different type of fibers or contain an inorganic substance such as titanium oxide used in the polyester, when the polyester is in the form of a film, BHET may be mixed with a different type of a film material and contain a lubricant used in the polyester, when the polyester is another molded product such as a bottle, BHET may be crushed and mixed with another type of material such as polyethylene used in a cover portion or bottom portion or mixed with a different type of material such as paper or other plastic used in a label. These are rather general situations. However, according to the result of studies conducted by the present inventors, a high-quality material of interest can be obtained by using a conventionally known technique such as liquid-liquid separation or solid-liquid separation and above-described various techniques included in the present invention as required.

EXAMPLES

The following examples are provided for the purpose of further illustrating the present invention but are in no way to be taken as limiting.

Example 1

64 kg of crashed flakes of a used PET bottle (made from a polyethylene terephthalate resin) and 450 kg of ethylene glycol (to be abbreviated as EG hereinafter) were charged into a 1 m$^3$ autoclave equipped with a stirrer, 0.32 kg of caustic soda (NaOH) was added as an ester exchange catalyst, depolymerization was carried out for 3.3 hours while low-boiling substances such as a small amount of water were distilled off at 220° C. and 0.15 MPa to prepare absolution containing EG as the main solvent and bis-β- hydroxyethyl terephthalate (to be abbreviated as BHET hereinafter) as the main solute. The solution was filtered to remove a small amount of impurities, cooled to a temperature of 55° C., and decolorized with activated carbon to obtain 510 kg of a solution. The total cation content (weight ratio) was 2,660 ppm and the total anion content was 23 ppm based on the concentrated solute (crude BHET) in the solution.

210 kg of this solution was decationized with a cation exchange resin (of Organo Co., Ltd., Amberlite IR120-B) and then deanionized with an anion exchange resin (of Organo Co., Ltd., Amberlite IRA-400) at a temperature of 55° C. The total cation content was 8.4 ppm and the total anion content was 1.0 ppm based on crude BHET in the solution after deionization. This decationized and deanionized solution was divided into two parts. 105 kg of one part was cooled to 3° C. with −5° C. brine in an agitation crystallization tank with a jacket to precipitate BHET which was then separated into precipitated BHET and EG by a basket type centrifugal separator to obtain a wet BHET cake. The solid content of this cake was 63 wt %. This cake was heated at 90 to 100° C., dissolved and charged into a 200l autoclave equipped with a stirrer and vacuum generator, and EG was distilled off at 135° C. and 10,670 Pa (80 mmHg) until the EG content of the solution became 20 wt %. This was concentrated with a vacuum thin film evaporator having a heat transfer area of 0.5 m$^2$ at 150° C. and 200 Pa (1.5 mmHg) until the total content of substances having a lower boiling point than BHET became 0.5 wt % to obtain 14.1 kg of a composition comprising crude BHET as the main ingredient. This is designated as (A).

The composition (A) comprising crude BHET as the main ingredient was distilled with a molecular distiller having a heat transfer area of 0.5 m2 at 200° C. and 24 Pa (0.18 mmHg) to obtain purified BHET. The operation results such as yield and the quality analysis values of purified BHET are shown in Table 1.

Thereafter, 500 g of this obtained purified BHET was charged into a 1,000-ml glass polymerizer equipped with a stirrer and heated at 130° C. in an N$_2$ gas atmosphere to melt BHET and an EG solution of hexagonal germanium dioxide was added to formed polyethylene terephthalate (to be abbreviated as PET hereinafter) as a polymerization catalyst in an amount of 140 ppm. These were gradually heated to the boiling point (197° C.) of EG and maintained at that temperature for 45 minutes to form a PET oligomer which was then polycondensed by gradually heating at 280° C. and 90 Pa (0.7 mmHg) over about 2 hours to obtain PET. The quality analytical values of the obtained PET are shown in Table 2.

The quality of purified BHET obtained from the crude BHET composition (A) before molecular distillation was extremely excellent in terms of optical density which has deep connection with the degree of coloring, the purity of BHET and the total content of MHET other than BHET and oligomer. The purified BHET yield of the molecular distillation operation is high, the formation rate of a by-produced oligomer is markedly small, and what accumulates in the distiller to prevent the operation is rarely formed. Examples 2 to 4

370 kg of EG was added as a raw material to 53 kg of each of two different types of flakes of used PET bottles (made from a PET resin) recovered from different sources to carry out depolymerization in the same manner as in Example 1 using 0.27 kg of sodium methylate in place of caustic soda as a depolymerization catalyst, and the obtained solutions were filtered and decolorized with activated carbon to obtain 420 kg of a crude BHET solution each. The total cation contents of the solutions were 2,000 ppm and 2,050 ppm and the total anion contents were 20 ppm and 22 ppm based on the crude BHET in the solutions.

Two different solutions were totally decationized and deanionized at 55° C. The ion exchange resins used for decationization and deanionization were the same as in Example 1. The total cation contents of the ionized solutions were 8 ppm and 12 ppm and the total anion contents were 0 ppm and 1.0 ppm based on the crude BHET in the solutions. The decationized and deanionized solutions were each divided into two parts. 210 kg of one part was crystallized to separate BHET in the same manner as in Example 1 so as to obtain wet BHET cakes which were dissolved by heating and concentrated under vacuum using an autoclave and a thin film evaporator until the total content of substances having a lower boiling point than BHET became 0.5 wt % or less. The amounts of the obtained compositions containing crude BHET as the main ingredient were 28.1 kg and 28.0 kg. These crude BHET's are designated as (F) and (G). The solvent EG and other low-boiling substances were distilled off from 210 kg of the other part without crystallization and the resulting solutions were concentrated with the same apparatus under the same temperature and pressure conditions as in the case of the crude BHET (F). The amounts of the obtained crude BHET compositions were 35.2 kg. These are designated as crude BHET (H).

The three compositions (F), (G) and (H) comprising crude BHET as the main ingredient were distilled with a molecular distiller having a heat transfer area of 0.5 m$^2$ by the same method under the same conditions as in Example 1 successively to obtain purified BHET's. The operation results such as yield and the quality analytical values of the purified BHET's are shown in Table 1 as Example 2 to 4. Thereafter, 500 g of each of the obtained purified BHET's was polycondensed by almost the same method under almost the same conditions as in Example 1. The quality analytical values of the obtained PET's are shown in Table 2.

The qualities of purified BHET's obtained from the crude BHET compositions (F), (G) and (H) before molecular distillation as Examples 2, 3 and 4 were extremely excellent in terms of optical density, whiteness, the purity of BHET and the total content of impurities. The purified BHET yield of the molecular distillation operation was high and the amount of the formed oligomer was considerably small.

TABLE 1

|  |  | Ex. 1 | Ex. 2 | Ex. 3 | Ex. 4 |
| --- | --- | --- | --- | --- | --- |
| composition supplied into molecular distiller |  | (A) | (F) | (G) | (H) |
| operation results | yield amount of purified BHET (kg) | 13.8 | 27.5 | 27.3 | 34.2 |
|  | yield rate of purified BHET (%) | 98.3 | 98.2 | 98.0 | 97.7 |

TABLE 1-continued

| | composition supplied into molecular distiller | Ex. 1 (A) | Ex. 2 (F) | Ex. 3 (G) | Ex. 4 (H) |
|---|---|---|---|---|---|
| | amount of formed oligomer (kg) | 0.06 | 0.10 | 0.12 | 0.18 |
| | formation rate of oligomer (%) | 0.5 | 0.4 | 0.5 | 0.6 |
| quality analytical values | optical density | 0.005 | 0.000 | 0.003 | 0.004 |
| | acid value (KOH mg/g) | 0.3 | 0.3 | 0.4 | 0.5 |
| | saponification value (KOH mg/g) | 440 | 440 | 438 | 438 |
| | melting point (° C.) | 112 | 112 | 112 | 112 |
| | whiteness (L/a/b) | 98.8/−0.6/0.5 | 98.7/−0.5/0.3 | 98.2/−0.6/0.5 | 98.4/−0.4/0.5 |
| | total cation content (ppm) | 0.5 | 0.4 | 0.5 | 0.7 |
| | total anion content (ppm) | 0 | 0 | 0.1 | 0 |
| | BHET content (wt %) | 99.0 | 99.1 | 98.8 | 95 |
| | MHET content (wt %) | 0.12 | 0.12 | 0.15 | 0.19 |
| | oligomer content (wt %) | 0.07 | 0.05 | 0.06 | 0.07 |

Ex. = Example

TABLE 2

| BHET composition subjected to polycondensation before distillation | Ex. 1 (A) | Ex. 2 (F) | Ex. 3 (G) | Ex. 4 (H) |
|---|---|---|---|---|
| intrinsic viscosity (IV) | 0.680 | 0.691 | 0.684 | 0.676 |
| diethylene glycol content (wt %) | 0.9 | 1.0 | 1.0 | 1.1 |
| amount of carboxyl terminal group (µeq/g) | 8.0 | 7.0 | 9.0 | 10.0 |
| whiteness (surface of crystallized sample L/a/b) | 91.0/−0.7/0.8 | 90.9/−0.6/0.2 | 90.2/−0.7/0.5 | 90.3/−0.5/0.8 |

Ex. = Example

Examples 5 to 9 and Comparative Example 1

Depolymerization was carried out using as raw materials 64 kg of little contaminated and non-colored waste PET (partially containing a low polymer) which was collected from the steps of polycondensing and spinning PET produced from high-purity terephthalic acid and EG as raw materials by a direct polymerization method and the step of molding a film or bottle to be formed into chips or small blocks through such processes as re-melting, cutting and crushing, 450 g of EG and 0.32 kg of caustic soda as a catalyst by almost the same method under almost the same conditions as in Example 1. Approximately 10 kg of EG was distilled off together with a small amount of a volatile component in the reaction step. The total content of cations dissolved in 504 kg of a crude BHET solution containing the obtained EG as the main solvent was 2,450 ppm and the total content of anions was 10 ppm based on crude BHET as the solute.

This solution was filtered to remove trace amounts of inorganic additives and impurities, the temperature was elevated to 55° C., and the solution was divided into some parts which were then supplied to the purification steps of FIG. 1 to obtain six compositions (J) to (O) containing crude BHET as the main ingredient. The amount of each composition acquired was about 11 to 14 kg and the content of each substances having a lower boiling point than BHET was about 0.5 wt %. All the purification steps used were carried out with almost the same equipment under almost the same conditions as in Example 1 in accordance with the method of Example 1. The step of concentrating and distilling off low-boiling substances is included in the end of the step of obtaining six compositions in the division purification process diagram of FIG. 1 as a step continuing thereto. The content of ions after the deionization step is shown below the step in the figure.

The six compositions (J) to (O) comprising crude BHET as the main ingredient were distilled with a molecular distiller having a heat transfer area of 0.5 m² by the same method under the same conditions as in Example 1 successively to obtain purified BHET's. The operation results such as yield and the quality analytical values of purified BHET's are shown in Table 3 as Examples 5 to 9 and Comparative Example 1. Thereafter, 500 g of each of the obtained purified BHET's was polycondensed by almost the same method under almost the same conditions as in Example 1. The quality analytical values of the obtained PET's are shown in Table 4.

The qualities of purified BHET's obtained from the crude BHET compositions (J) to (N) before molecular distillation as Examples 5 to 9 were extremely excellent in terms of optical density, whiteness, the purity of BHET and the total content of impurities. The purified BHET yield of the molecular distillation operation was high and the amount of the formed oligomer was considerably small. Meanwhile, in Comparative Example 1 in which the deionization step was not carried out, purified BHET was inferior in such quality as optical density and the results of molecular distillation operation. In Comparative Example 1, the amounts of an inorganic substance and a high-melting oligomer accumulated in the molecular distiller were large and long-time operation was difficult.

As for the quality of PET obtained by polycondensing BHET purified by distillation, Examples 5 to 9 were markedly excellent in terms of whiteness and apparently superior to Comparative Example 1 in terms of polymerizability (IV), the content of diethylene glycol and the amount of a carboxyl terminal group which is one of indices for heat stability. It is understood that the quality of the purified BHET used (optical density of 0.006 or less) is extremely excellent as a PET raw material.

In Examples 5 to 9 and Comparative Example 1, waste which was produced from a polyester production plant and little contaminated was used as a starting material. It is understood from these examples that there is a case where it is possible to omit the crystallization step and/or decolorization step or the deanionization step.

TABLE 3

| composition supplied into molecular distiller | Ex. 5 (J) | Ex. 6 (K) | Ex. 7 (L) |
|---|---|---|---|
| operation results — yield amount of purified BHET (kg) | 11.0 | 13.4 | 11.1 |
| yield rate of purified BHET (%) | 98.0 | 97.8 | 98.1 |
| amount of formed oligomer (kg) | 0.04 | 0.08 | 0.06 |
| formation rate of oligomer (%) | 0.4 | 0.6 | 0.5 |
| quality analytical values — optical density | 0.001 | 0.003 | 0.004 |
| acid value (KOH mg/g) | 0.3 | 0.4 | 0.4 |
| saponification value (KOH mg/g) | 440 | 440 | 439 |
| melting point (° C.) | 112 | 112 | 112 |
| whiteness (L/a/b) | 98.6/−0.4/0.3 | 98.5/−0.5/0.4 | 98.3/−0.6/0.5 |
| total cation content (ppm) | 0.4 | 0.5 | 0.4 |
| total anion content (ppm) | 0.1 | 0.2 | 0.1 |
| BHET content (wt %) | 99.2 | 99.0 | 99.2 |
| MHET content (wt %) | 0.14 | 0.15 | 0.12 |
| oligomer content (wt %) | 0.04 | 0.04 | 0.05 |

| composition supplied into molecular distiller | Ex. 8 (M) | Ex. 9 (N) | C. Ex. 1 (O) |
|---|---|---|---|
| operation results — yield amount of purified BHET (kg) | 13.6 | 11.2 | 7.4 |
| yield rate of purified BHET (%) | 97.7 | 97.4 | 65.0 |
| amount of formed oligomer (kg) | 0.08 | 0.09 | 1.09 |
| formation rate of oligomer (%) | 0.6 | 0.5 | 9.5 |
| quality analytical values — optical density | 0.006 | 0.005 | 0.009 |
| acid value (KOH mg/g) | 0.5 | 0.6 | 1.2 |
| saponification value (KOH mg/g) | 439 | 439 | 437 |
| melting point (° C.) | 112 | 112 | 111 |
| whiteness (L/a/b) | 98.0/−0.8/0.7 | 98.1/−0.7/0.5 | 97.6/−0.9/1.5 |
| total cation content (ppm) | 0.6 | 0.5 | 1.7 |
| total anion content (ppm) | 0.2 | 0.4 | 1.5 |
| BHET content (wt %) | 99.0 | 98.8 | 97.0 |
| MHET content (wt %) | 0.16 | 0.16 | 0.18 |
| oligomer content (wt %) | 0.05 | 0.07 | 0.06 |

Ex. = Example
C. Ex. = Comparative Example

TABLE 4

| BHET composition subjected to polycondensation before distillation | Ex. 5 (J) | Ex. 6 (K) | Ex. 7 (L) |
|---|---|---|---|
| intrinsic viscosity (IV) | 0.693 | 0.685 | 0.688 |
| diethylene glycol content (wt %) | 0.8 | 1.0 | 0.8 |
| amount of carboxyl terminal group (μeq/g) | 7.5 | 10.0 | 8.5 |
| whiteness (surface of crystallized sample L/a/b) | 91.4/−0.4/0.3 | 90.0/−0.6/0.4 | 90.0/−0.7/0.6 |

| BHET composition subjected to polycondensation before distillation | Ex. 8 (M) | Ex. 9 (N) | C. Ex. 1 (O) |
|---|---|---|---|
| intrinsic viscosity (IV) | 0.680 | 0.677 | 0.666 |
| diethylene glycol content (wt %) | 1.1 | 1.2 | 1.4 |
| amount of carboxyl terminal group (μeq/g) | 10.6 | 11.5 | 14.0 |
| whiteness (surface of crystallized sample L/a/b) | 90.0/−0.8/1.0 | 90.1/−0.7/0.7 | 89.6/−0.9/2.5 |

Ex. = Example
C. Ex. = Comparative Example

Comparative Examples 2 and 3

332 g of high-purity terephthalic acid which was commercially available and 149 of EG were added to a 1-liter small-sized autoclave equipped with a packed column and stirrer, the temperature and pressure were first set to 220° C. and 0.15 MPa, respectively, and then the temperature was gradually elevated while water generated was removed. The esterification stage was completed in about 3 hours and germanium dioxide dissolved in EG was added as a polymerization catalyst to a PET oligomer which reached a temperature of 270° C. in an amount of 140 ppm based on the formed PET. The temperature was gradually elevated to 280° C. and the pressure was reduced to 90 Pa (0.7 mmHg) to carry out polycondensation for about 2 hours. The quality analytical values of the obtained PET are shown in Table 5 as Comparative Example 2.

Thereafter, 388 g of commercially available dimethyl terephthalate, 174 kg of EG and 0.12 g of cobalt acetate were added to the same autoclave as in Comparative Example 2 and the temperature was gradually elevated from the boiling point (197° C.) of EG. The temperature was elevated to 260° C. in about 3 hours while generated methanol was removed to complete an ester exchange reaction and then 0.07 g of phosphoric acid and the same amount of germanium dioxide as in Comparative Example 2 were added as polymerization catalysts. The temperature was gradually elevated to 280° C. and the pressure was reduced to 90 Pa (0.7 mmHg) to carry out polycondensation for about 2 hours to obtain PET. The quality analytical values of the obtained PET are shown in Table 5 as Comparative Example 3.

The quality of PET obtained from commercially available high-purity terephthalic acid or dimethyl terephthalate was inferior in terms of whiteness (b value), the amount of a carboxyl group and the content of diethylene glycol. Particularly, PET of Comparative Example 3 which was obtained from dimethyl terephthalate as a raw material was unsatisfactory in terms of whiteness though a bluing effect (reduction of b value) caused by the violet color of a cobalt compound used as an ester exchange catalyst was observed.

TABLE 5

| | C. Ex. 2 | C. Ex. 3 |
|---|---|---|
| intrinsic viscosity (IV) | 0.660 | 0.654 |
| diethylene glycol content (wt %) | 2.3 | 2.2 |
| amount of carboxyl terminal group (μeq/g) | 15.5 | 23.0 |
| whiteness (surface of cryallized sample L/a/b) | 90.1/−0.8/2.6 | 88.5/−1.2/3.2 |

C. Ex. = Comparative Example

Effect of the Invention

The present invention makes it clear that purified BHET having an optical density of 0.006 or less provides high-quality PET which is excellent in terms of purity, whiteness and transparency.

The purified BHET of the present invention can be obtained from crude BHET which has been deionized to a specific content by high-vacuum distillation such as molecular distillation. The purified BHET of the present invention can also be obtained even by the method of depolymerizing collected PET waste containing a wide variety of impurities in large quantities by using decolorization and/or crystallization as required.

The present invention can be advantageously used for the recycling of high-quality pet molded products such as fibers, films and bottles and purified BHET which is a high-quality monomer.

What is claimed is:

1. Bis-β-hydroxyethyl terephthalate having (i) an optical density measured in a 10 wt. % methanol solution at a measurement wavelength of 380 nm and a cell optical path length of 10 mm of 0.000 to 0.006, (ii) cation content of 15 ppm or less, (iii) anion content of 1 ppm or less, and (iv) purity of 98 wt. % or more.

2. Process for producing the bis-β-hydroxyethyl terephthalate of claim 1, comprising the steps of:

(i) depolymerizing a collected post-consumer polyethylene terephthalate with ethylene glycol to form depolymerized products containing bis-β-hydroxyethyl terephthalate, (ii) carrying out decationization and/or deanionization for the depolymerized products formed in the step (i) to form deionized products having total content of cations and anions of 40 ppm or less, and (iii) carrying out molecular distillation for the deionized products formed in the step (ii) at 160° to 220° C. under a pressure of 70 Pa or less.

* * * * *